(12) United States Patent
Schreiber et al.

(10) Patent No.: US 11,013,260 B1
(45) Date of Patent: May 25, 2021

(54) STANDALONE HERB PROCESSING, VAPORIZING, AND ADMINISTRATION APPARATUSES, SYSTEMS, AND METHODS

(71) Applicant: CANNAHEAL LLC, Livingston, NJ (US)

(72) Inventors: Jeremy Schreiber, Livingston, NJ (US); Nicholas Sanjines, Powell, TN (US); Harrison Seidner, Livingston, NJ (US)

(73) Assignee: CANNAHEAL LLC, Livingston, NJ (US)

( * ) Notice: Subject to any disclaimer, the term of this patent is extended or adjusted under 35 U.S.C. 154(b) by 0 days.

(21) Appl. No.: 17/073,028

(22) Filed: Oct. 16, 2020

(51) Int. Cl.
| | |
|---|---|
| *A24F 40/20* | (2020.01) |
| *A24B 7/04* | (2006.01) |
| *A24F 40/85* | (2020.01) |
| *A24F 40/485* | (2020.01) |
| *A61M 11/04* | (2006.01) |

(52) U.S. Cl.
CPC ............ *A24F 40/20* (2020.01); *A24B 7/04* (2013.01); *A24F 40/485* (2020.01); *A24F 40/85* (2020.01); *A61M 11/041* (2013.01)

(58) Field of Classification Search
None
See application file for complete search history.

(56) References Cited

U.S. PATENT DOCUMENTS

| | | | |
|---|---|---|---|
| 9,149,586 B2 | 10/2015 | Shen et al. | |
| 9,427,022 B2 | 8/2016 | Levin et al. | |
| 2016/0331913 A1 | 11/2016 | Bourque | |
| 2017/0245546 A1 | 8/2017 | Huang | |
| 2017/0367408 A1* | 12/2017 | Pang | A24B 7/04 |
| 2019/0208823 A1* | 7/2019 | Raichman | A24F 40/40 |

OTHER PUBLICATIONS

Yocan iShred Vaporizer, https://www.yocanvaporizer.com/products/yocan-ishred-vaporizer, Oct. 16, 2020, 5 pgs.

* cited by examiner

*Primary Examiner* — Michael H. Wilson
*Assistant Examiner* — Katherine A Will
(74) *Attorney, Agent, or Firm* — Greenberg Traurig, LLP

(57) ABSTRACT

An herb vaporizing apparatus includes an herb receiving port, a grinder to grind the herb, and a heating chamber for heating the ground herb to create a vapor. A first end of the heating chamber is positioned closer to a top of the apparatus than a second end of the heating chamber, such that the ground herb generally moves in at least a partially downward direction as it travels through the heating chamber. The apparatus further includes a screw feeder positioned within the heating chamber that rotates and moves the ground herb within the heating chamber. The apparatus further includes an air pump for pumping vapor out of the heating chamber and a valve positioned along an airway between the heating chamber and a vapor output. The valve permits air and the vapor to move from the heating chamber to the vapor output only while the air pump is activated.

17 Claims, 9 Drawing Sheets

US 11,013,260 B1

STANDALONE HERB PROCESSING, VAPORIZING, AND ADMINISTRATION APPARATUSES, SYSTEMS, AND METHODS

BACKGROUND

Many people use herbs, oils, or other substances along with devices for creating vapors. For example, certain herbs, oils, or other substances may be heated to create vapors that may be used for medicinal purposes, for creating scents in a room, or for any other purpose. The vapors created may, for example, be inhaled by a user.

SUMMARY

An illustrative standalone herb processing, vaporizing, and administration apparatus includes an herb receiving port configured to receive herb, a grinder configured to grind the herb received at the herb receiving port into ground herb, and a heating chamber configured to receive the ground herb. The heating chamber is configured to heat the ground herb, to thereby create a vapor. The heating chamber also comprises a first end at which the ground herb is initially received, and a second end at which the ground herb is output from the heating chamber. The first end of the heating chamber is positioned closer to a top of the standalone herb processing, vaporizing, and administration apparatus than the second end of the heating chamber, such that the ground herb generally moves in at least a partially downward direction as it travels through the heating chamber. The standalone herb processing, vaporizing, and administration apparatus further includes a screw feeder positioned within the heating chamber, the screw feeder configured to rotate and thereby move the ground herb within the heating chamber. The standalone herb processing, vaporizing, and administration apparatus further includes an air pump configured to pump the vapor out of the heating chamber to a vapor output device and a valve positioned along an airway between the heating chamber and the vapor output device. The valve is configured to permit air and the vapor to move from the heating chamber to the vapor output device only while the air pump is activated.

An illustrative apparatus includes a heating chamber configured to receive ground herb. The heating chamber is configured to heat the ground herb. The heating chamber further includes a first end at which the ground herb is initially received, and a second end at which the ground herb is output from the heating chamber. The apparatus further includes a screw feeder positioned within the heating chamber, the screw feeder configured to rotate and thereby move the ground herb within the heating chamber.

An illustrative apparatus includes a heating chamber configured to receive ground herb. The heating chamber is configured to heat the ground herb. The heating chamber further includes a first end at which the ground herb is initially received, and a second end at which the ground herb is output from the heating chamber. The first end of the heating chamber is positioned closer to a top of the standalone herb processing, vaporizing, and administration apparatus than the second end of the heating chamber.

An illustrative apparatus includes a heating chamber configured to receive ground herb and heat the ground herb, to thereby create a vapor. The apparatus further includes an air pump configured to pump the vapor out of the heating chamber to a vapor output device. The apparatus further includes a valve positioned along an airway between the heating chamber and the vapor output device. The valve is configured to permit air and the vapor to move from the heating chamber to the vapor output device only while the air pump is activated.

DETAILED DESCRIPTION

Figure 1:
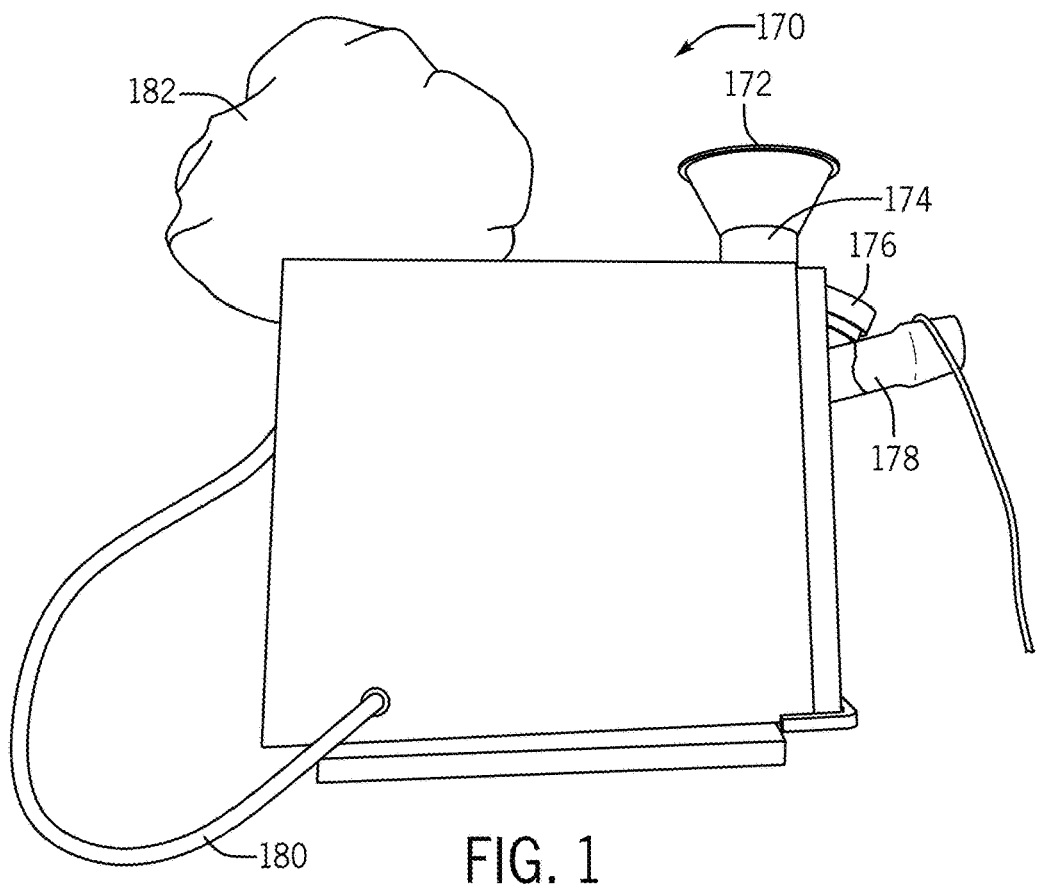
FIG. 1 is a perspective view of an example standalone herb processing, vaporizing, and administration apparatus, in embodiments.

Various apparatuses, methods, and systems for standalone herb processing, vaporizing, and administration devices are described herein. In particular, the embodiments herein relate to a device that is user friendly and automates as many aspects as possible of a process of processing herb for vaporizing (e.g., grinding), vaporizing the herb (e.g., heating ground herb to specified temperature), and administering/delivering the resulting vapor to a user. Such apparatuses, methods, and systems may further be implemented, at least in part, using a processor or controller that executes software code or instructions stored on a memory (e.g., a computer implemented method) to control various aspects of a standalone herb processing, vaporizing, and administration device and to further automate the use and maintenance of such a device to provide a user-friendly product. Any type of herb or other product that is suitable to vaporize may be used according to the various systems, apparatuses, and methods described herein. For example, herbs such as cannabis, damiana, catnip, valerian, passion flower, lavender, lemon balm, wild lettuce, chamomile, hops, gunpowder green tea, blue lotus, yerba mate, calea zacatechichi, peppermint, thyme, basil, eucalyptus, rosemary, sage, anise, jasmine, rose, mugwort, clove, ginseng, morning glory, St. John's Wort, hibiscus, burdock root, coffee, hemp, tobacco, or any other plant, herb, or oil may be vaporized as described herein.

As just one example, individuals or users that have limited mobility or dexterity due to age, a medical condition, etc. may benefit from the embodiments of the standalone herb processing, vaporizing, and administration devices described herein. Traditional ways of preparing herb and vaporizing it for use may be difficult for such individuals, requiring them to rely on the assistance of a caregiver or, left on their own, to complete aspects of preparing and vaporizing herb in a suboptimal way.

For example, a standalone herb processing, vaporizing, and administration device may receive dried herb into a hopper or other herb receiving port. The device may initiate a process of processing and vaporizing the herb automatically (e.g., if the device includes a sensor for detecting that herb has been put in the device) or upon a minimal interaction from a user (e.g., at the push of a button). In an example with a push button, it may be large and easy to push so that users with limited mobility or dexterity may push the button to begin the processing and vaporization process of the herb. In addition, the hopper of the device may be pre-loaded with a significant amount of herb that will last for multiple uses. In this way, if a user is not able to or otherwise needs help loading the herb into the hopper, enough herb may be placed in the hopper for multiple uses, such that less assistance is needed for the user. The device may then only process and vaporize a predetermined portion of the herb during each use.

Upon actuation of the standalone device, a small portion of the herb that has been loaded into the hopper may be transferred to a grinder powered by a motor, where the herb may be automatically ground without further effort by the user. In many instances, grinders traditionally used to grind herb may be manually powered, and are often separate from any vaporizing device. As such, a user may have to perform several steps with their hands to put the herb in a grinder, exert a significant degree of force to cause the grinder to turn or otherwise move to grind the herb, and then transfer the ground herb to a vaporizer. In the embodiments described herein, the herb may be ground automatically using a motor, and the ground herb may then be automatically passed to a portion of the device that heats and vaporizes the ground herb. In this way, the herb may be processed with minimal interaction from the user.

Once the herb is properly heated to create a vapor from the herb, spent herb may be automatically removed from the heating chamber to a spent herb container. The spent herb container may advantageously be sized to hold spent herb from multiple uses of the device, so that the user does not have to frequently empty the spent herb container. This again provides advantages for users with reduced mobility or dexterity, as the user would not have to empty the spent herb container during most uses of the device. The vaporizer may also include an air pump for moving the vapor created to an output device, such as a balloon or whip. In addition, the standalone device may also be capable of performing partially or fully automated cleaning processes, so that the standalone device can be easily cleaned by a user of limited mobility or dexterity.

To further enhance the usability of the herb processing, vaporizing, and administration devices described herein, they may be controlled using many various types of technology. For example, the devices may be controlled or actuated using a wireless remote control, an application on another device (e.g., on a smartphone, tablet, laptop, etc.), a remote switch, on-device buttons or dials, other wireless communications such as Bluetooth, an eye tracking device, an application programming interface (API), and/or voice control.

Therefore, further described herein are high quality, fully integrated, turn-key herb vaping devices that may be specifically advantageous for those with physical limitations to enable easy, hands-free marijuana vaping sessions, to use independently without assistance of a caregiver.

FIG. 1 is a perspective view of an example standalone herb processing, vaporizing, and administration apparatus, which includes a vaporizing device 170. The vaporizing device 170 includes a hopper 172 into which herb may be inserted. The hopper 172 may hold a significant amount of herb that is enough for multiple uses or sessions of vaporizing the herb. The vaporizing device 170 may include a grinder (not shown) at a location 174 for grinding the herb. In various embodiments, the amount of herb that is ground for a single use or session may be controlled based on how long the grinder is turned on. That is, the grinder will move herb from the hopper to an herb entry port 176 and/or a heating chamber (not shown in FIG. 1) at a particular rate, so the amount of herb ground and moved from the hopper may be controlled by controlling how long the grinder is on. Accordingly, an amount of herb ground may also be adjusted by adjusting how long the grinder is on.

In other embodiments, other mechanical or electromechanical components may be used to control how much herb is ground per use. For example, a rotatable door or louver at the base of the hopper may be opened to allow a certain amount of herb into the grinder. In other embodiments, other methods of controlling the amount of herb that moves from the hopper to the grinder may be used. In still further embodiments, a user may put the amount of herb they desire for a single session in the hopper, and all the herb in the hopper may be permitted to pass to the grinder. In still further embodiments, the herb may be pre-packaged in a single serve container or cartridge. Such single serve containers or cartridges may be loaded into the vaporizing device 170 instead of putting loose herb into a hopper. The single serve containers or cartridges may then be used one per use or session by the vaporizing device 170 by breaking open the containers or cartridges and causing the herb inside to pass to the grinder. Accordingly, many different methods may be used to load herb into the vaporizing device and pass a portion or all of that herb to a grinder and heating chamber for vaporizing.

The vaporizing device 170 further includes a motor 178. The motor 178 may be used to turn a rotatable grinder to grind the herb. In addition, the motor 178 may also be used to turn a feature in a heating chamber of the vaporizing device 170 to move or otherwise disturb ground herb in the heating chamber. This may ensure that the ground herb is heated and vaporized evenly without burning herb and/or failing to vaporize portions of the ground herb. The feature may be, for example, a screw feeder as shown in and described below with respect to FIGS. 2-4.

Once the spent herb is vaporized, an air pump (not shown in FIG. 1) may be actuated to move air and vapor from the heating chamber to a vapor output device. In the example of FIG. 1, the output device is an output tube 180 connected to a balloon 182. The balloon 182 may therefore store vapor, let it cool, etc. until a user inhales it from the balloon either directly or indirectly from a whip, mouthpiece, mask, etc.

The vaporizing device 170 may be designed to sit on a table, floor, desk, or anywhere else. Portions of the vaporizing device 170 that are accessed by the user may be placed in a location that makes access by different types of users (e.g., users in wheelchairs) easy depending on what surface the vaporizer device 170 is sitting (e.g., what shape of object it is sitting on, height of object, etc.). The vaporizing device may also be configurable for mounting to a wheelchair, so that an individual with limited mobility may have it with them as they move around in a wheelchair. Any user inputs that the user in the wheelchair may interact with may be specifically designed and placed on the vaporizer device with the person in the wheelchair in mind, so that those user inputs may be easily accessed.

Figure 2:
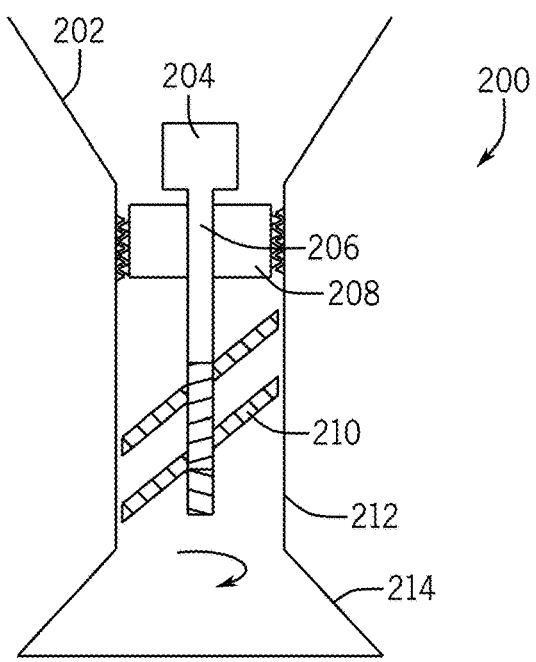
FIG. 2 is a cross-sectional view of an example heating chamber, screw feeder, and grinder of a standalone herb processing, vaporizing, and administration apparatus, in embodiments.

FIG. 2 is a cross-sectional view 200 of an example heating chamber 212, screw feeder 210, and grinder 208 of a standalone herb processing, vaporizing, and administration apparatus, in embodiments. The heating chamber 212, screw feeder 210, and grinder 208 configuration may be used, for example in the vaporizing device 170 of FIG. 1. A hopper 202 may receive herb, and that herb may pass to a grinder 208. The grinder 208 may be a burr grinder, conical burr grinder, or may be a different type of grinder. The grinder 208 is configured such that herb in the hopper 202 cannot pass into the heating chamber 212 unless the grinder 208 is on and is grinding the herb. In other words, the herb may be too large to pass by the grinder 208 without being ground. In this way, the amount of herb that passes into the heating chamber may be controlled based on how long the grinder 208 is actuated.

The grinder 208 is configured to grind the herb by rotating, and teeth on the grinder 208 and the inner surface of the heating chamber 212 grind the herb into smaller pieces of herb that may pass into the heating chamber. The grinder 208 may be rotated by a motor 204. The motor 204 is connected to a shaft 206 that is connected to both the grinder 208 and the screw feeder 210. Accordingly, both the grinder 208 and the screw feeder 210 may be turned by the same motor 204. In some embodiments, it may be desirable to turn the grinder 208 and the screw feeder 210 at different rates or at different times. In such embodiments, multiple motors may be used. To turn the grinder 208 and the screw feeder 210 at different rates, a single motor may be used along with a gear box being intermediate between a shaft of the single motor and at least one of the grinder 208 and the screw feeder 210, so that the grinder 208 and/or the screw feeder 210 may be rotated at different rates. The screw feeder 210 may be a drill bit, auger, screw conveyer, auger conveyer, or any other type of variable rate feeder.

The motor 204 may also be variable speed, so that the shaft 206 may be rotated at different rates as desired to control the rate at which herb is ground and/or at which ground herb is agitated or moved through the heating chamber 212. In various embodiments, multiple features that control the amount of herb that is ground and/or heated may be used. For example, a louver or other moveable mechanical door may be located between the hopper 202 and the grinder 208 to control how much herb is allowed into the grinder 208. Once the grinder 208 has been on and the door has been open for a predetermined amount of time, the door may close but the grinder 208 may continue to turn to finish grinding any herb that has already moved past the door. In this way, the motor 204 may also continue to cause the screw feeder 210 to rotate to agitate or move the herb within the heating chamber 212, without causing more herb to be ground and move from the hopper to the grinder 208 and the heating chamber 212.

The screw feeder 210 is configured to move the herb through the heating chamber 212. The end of the heating chamber 212 connected to the hopper 202 may also be oriented to be above or higher than an end of the heating chamber 212 connected to a spent herb outlet 214. In this way, gravity also may serve to help move herb or anything else in the heating chamber 212 (e.g., cleaning solution) toward the spent herb outlet 214. The screw feeder 210 in the example of FIG. 2 is therefore configured to lower the herb through the heating chamber 212 so that it can be gradually heated within the heating chamber thereby creating a vapor. As discussed herein, the motor 204 may be rotated at different rates and/or a gear box may be used to control the rate at which the screw feeder 210 moves. In this way, the rate at which the herb moves through the heating chamber 212 may be controlled so that the herb is in the heating chamber 212 for a desired amount of time for a given temperature so as to properly vaporize the herb.

In various embodiments, the screw feeder 210 may be configured differently or may be a different type of component than an screw feeder. For example, the screw feeder may instead be a rotatable paddle or mixer that agitates herb within the heating chamber 212. In such an embodiment, the heating chamber 212 may have a door at the end of the heating chamber 212 where it connects to the spent herb outlet 214 so that the herb cannot fall out of the heating chamber 212 until the door is opened. In another embodiment, a conveyor or similar mechanism may be used to move the herb through the heating chamber 212 at a particular rate.

Figure 3:
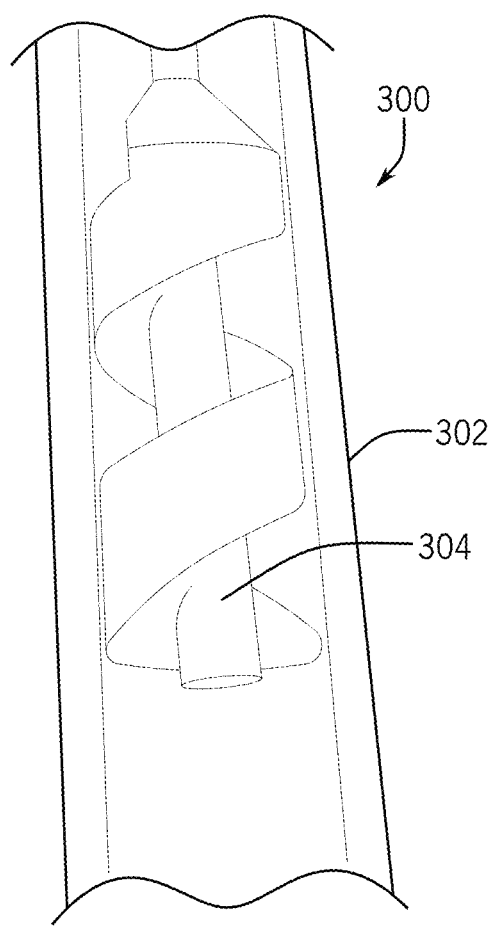
FIG. 3 is a partial perspective view of an example heating chamber and screw feeder of a standalone herb processing, vaporizing, and administration apparatus, in embodiments.

FIG. 3 is a partial perspective view of an example heating chamber 302 and screw feeder 304 of a standalone herb processing, vaporizing, and administration apparatus, in embodiments. In the example of FIG. 3, the heating chamber 302 is shown as transparent so that the screw feeder 304 is visible within the heating chamber 302.

Figure 4:
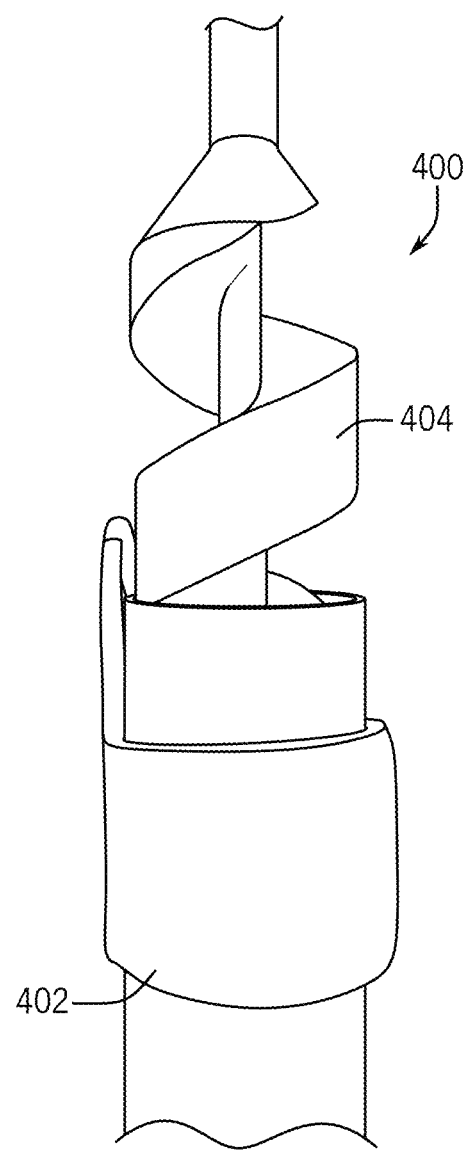
FIG. 4 is a partially exploded perspective view of an example heating chamber and screw feeder of the standalone herb processing, vaporizing, and administration apparatus of FIG. 1, in embodiments.

FIG. 4 is a partially exploded perspective view of an example heating chamber 402 and screw feeder 404 of the standalone herb processing, vaporizing, and administration apparatus of FIG. 1, in embodiments. The heating chamber 402 and/or the screw feeder 404 may be made of metal or other suitable material for conducting heat, so that herb within the heating chamber may be effectively heated as desired. As described herein, the screw feeder 404 may move ground herb from a first end of the heating chamber at which the ground herb is initially received to a second end at which the ground herb is output from the heating chamber. The second end (not pictured), may be connected to a spent herb container.

Figure 5:
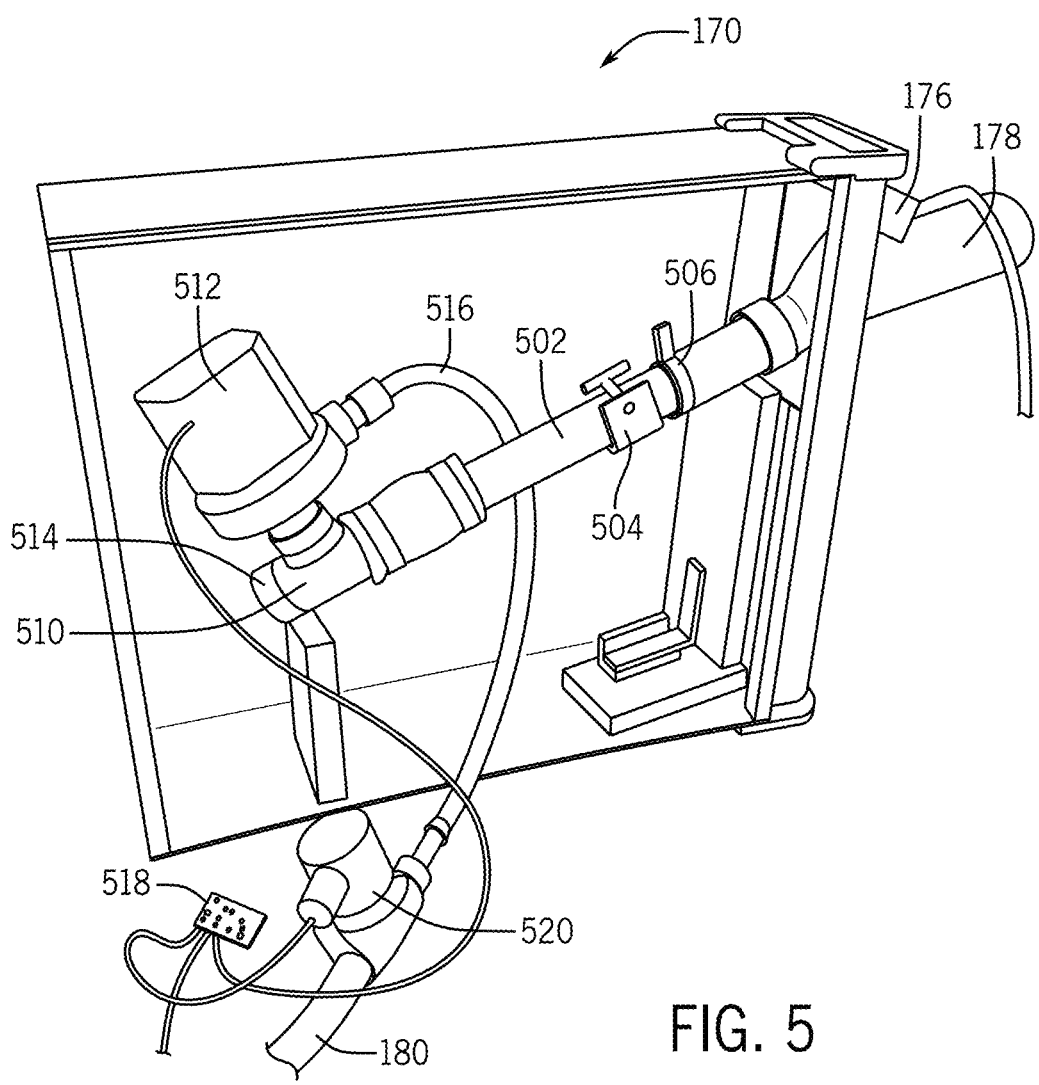
FIG. 5 is a partially exploded perspective view of the standalone herb processing, vaporizing, and administration apparatus of FIG. 1 with one side of the housing having been removed to reveal the internal components therein, in embodiments.

FIG. 5 is a partially exploded perspective view of the standalone herb processing, vaporizing, and administration apparatus of FIG. 1 with one side of the housing having been removed, in embodiments. In FIG. 5, various internal components of the vaporizing device 170 of FIG. 1 are visible. Those internal components include a heating chamber 502, a band heater clamp 504, a thermocouple 506, a spent herb outlet 510, an air pump 512, a moveable sealing component 514, air tubing 516 a controller 518, and a valve 520.

As described herein, herb may be moved from a hopper and/or grinder (not shown in FIG. 5) to the herb entry port 176 to pass into the heating chamber 502. The heating chamber 502 may be heated by a band heater (not shown in FIG. 5), which is held in place around the heating chamber 502 by a band heater clamp 504. The band heater may be controlled by and/or powered by the controller 518. In various embodiments, electrical components of the vaporizing device 170 may be powered by an auxiliary power and controlled by a processor or controller.

A temperature of the band heater and/or the heating chamber 502 may also be measured using the thermocouple 506. In this way, the temperature of the heating chamber 502 may be controlled based on feedback provided via the thermocouple 506. Accordingly, the heating chamber 502 may be heated to different temperatures for different amounts of time as desired or based on the type of herb used, the amount of herb in the heating chamber, the amount of time herb spends in the chamber (e.g., based on the rotation of an screw feeder within the chamber), etc.

After passing through the heating chamber 502, the spent herb may then pass to the spent herb outlet 510 located at a second end of the heating chamber 502. As is shown in FIG. 5, a first end of the heating chamber 502 that is connected to the herb entry port 176 is oriented higher than the second end of the heating chamber 502. The heating chamber 502 is cylindrical or tube shaped, and oriented at an angle between zero and ninety degrees with respect to a base of the vaporizing device. In some embodiments, the heating chamber 502 may be oriented at any degree from zero to ninety degrees, including angles such as 0 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, or 90 degrees. With the heating chamber 502 angled downward, the ground herb may generally move in at least a partially downward direction as it travels through the heating chamber 502.

The air pump 512 is connected to the spent herb outlet 510. The spent herb outlet 510 may be insulated from the heating chamber 502 so that it does not get as hot as the heating chamber 502. In this way, the vapor produced in the heating chamber 502 may not continue to heat while it is in the spent herb outlet 510 and/or may cool down in the spent herb outlet 510. The spent herb outlet 510 may also be shaped so that an air connection to the air pump 512 and/or the tubing 516 is placed so that spent herb cannot get into the tubing 516. Such a connection may also have a filter to allow air and vapor into the tubing but not any particulate matter such as the spent herb.

The moveable sealing component 514 may be moveable to allow spent herb to pass from the spent herb outlet 510 to a spent herb container (not shown in FIG. 5). The spent herb container may be able to hold a significant amount of spent herb or other material (e.g., cleaning solution), so that the spent herb container need not be emptied after each use of the vaporizer device 170. In various embodiments, the moveable sealing component 514 may be located or placed differently than as shown in FIG. 5, or additional moveable sealing components may be used. For example, a moveable sealing component may exist between the heating chamber 502 and the spent herb outlet 510, so that herb or other materials (e.g., cleaning solution) may be kept in the heating chamber 502 as desired. Any moveable sealing components, including the moveable sealing component 514 may be controlled via the controller 518 as desired. The controller 518 may therefore, as an example, control a heating element of the heating chamber 502 to heat the heating chamber 502 to a predetermined temperature and control an screw feeder within the heating chamber 502 to move the ground herb through the heating chamber 502, such that the ground herb is in the heating chamber 502 for a predetermined amount of time at a predetermined temperature.

The valve 520 may also be controllable by the controller 518. The valve 520 is positioned along an airway between the heating chamber and the vapor output device. In particular, the valve 520 may only allow air and vapor to flow one way—from the tubing 516 to the output tube 180. In addition, the valve 520 may be controllable so that when the valve 520 is open, air and vapor is allowed to flow from the tubing 516 to the output tube 180, but while the valve 520 is closed, no air is permitted to flow past the valve 520. Thus, the valve 520 may be a one-way controllable check valve. In various embodiments, other configurations of valves are possible.

The valve 520 may be controlled to only be open while the air pump 512 is operational. In this way, air and vapor may not pass through the valve 520 when it should not, and air and vapor may not pass from the output tube 180 to the tubing 516 at all. Such a configuration may be desirable for protecting a user and/or ensuring a quality of the vapor created by the vaporizing device 170. For example, while the heating chamber 502 is heating herb and creating vapor, it may be desirable to prevent that air from moving to the output tube 180 (e.g., by a user sucking air through a whip or mouthpiece) before the herb is completely vaporized. Furthermore, it may be desirable to keep air that is too hot (and therefore unsafe for a user) from passing to the output tube 180. Accordingly, the thermocouple 506 may be used to monitor a temperature of the heating chamber, and the controller may then only switch on the air pump 512 once the temperature has reached a level that is safe for the user. The valve 520 also prevents the user from blowing air into the system, which may cause the system to malfunction or work less efficiently. Similarly, the valve 520 also prevents air from outside the vaporizer from getting into the vaporizer and mixing with the vapor. In various embodiments, different types of valves may be used that have different functionalities. For example, one or more valves and/or air pumps may be configured to intake ambient air from outside of the closed system of the heating chamber 502 and the tubing 516. In this way, air may be mixed with vapor and sent to the output tube 180. This may be used to control a dose or amount of vapor received by the user, adjust the amount of vapor and fresh air mix for preference of the user, to reduce the harshness of vapor that reaches the user, reduce the temperature of vapor that reaches the user, or for any other desired purpose.

The valve 520 may further be electrically controlled by a processor or controller such as the controller 518. The valve 520 may therefore be an electrically controllable valve configured to switch between an open and a closed position as described herein. The valve 520 may therefore be electrically controllable to permit air and vapor to move from the heating chamber 502 to a vapor output device while the valve 520 is open, prevent air and vapor from moving from a vapor output device to the heating chamber 502 while the valve 520 is open, and prevent air and vapor from moving past the valve 520 in either direction while the valve 520 is closed. As described herein, the controller 518 may be further configured to control the valve 520 and the air pump 512 to simultaneously actuate, such that air and vapor move from the heating chamber 502 to a vapor output device only while the air pump 512 is activated.

Figure 6:
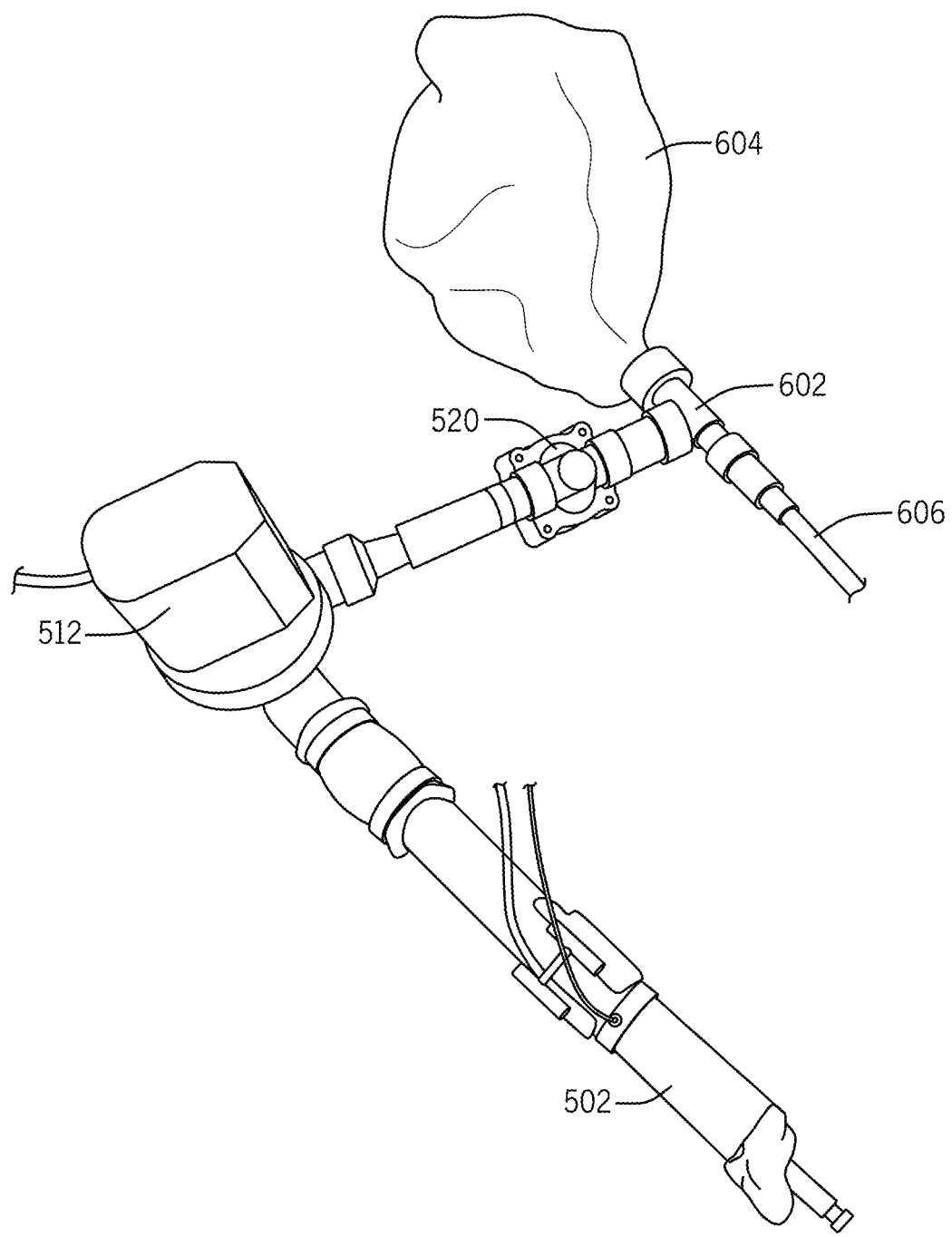
FIG. 6 is a partial perspective view of the heating chamber, air pump, valve, and vapor output device of the standalone herb processing, vaporizing, and administration apparatus of FIG. 1, in embodiments.

FIG. 6 is a partial perspective view of the heating chamber 502, air pump 512, valve 520, and vapor output device of the standalone herb processing, vaporizing, and administration apparatus of FIG. 1, in embodiments. In particular, the valve 520 is connected to t-joint 602 that connects to output tubing 606 and a balloon 604. In such a configuration, the output tubing 606 may be connected to a mouthpiece, whip, ventilator adapter, mask, etc. as desired for output of the vapor. The output tubing 606 or other output device may include a one-way valve that may be actuated when a user sucks air, for example. In this way, when the air pump is on and the valve 520 is open, vapor and air may move into the balloon for storage and not escape into ambient air via the output tubing 606. A user may receive air and vapor via the output tubing 606 either from air and vapor stored in the balloon 604 and/or as it is output from the valve 520. In various embodiments, a balloon may not be used, and some other vapor storage device (e.g., a bag) or no vapor storage device may be used.

Figure 7:
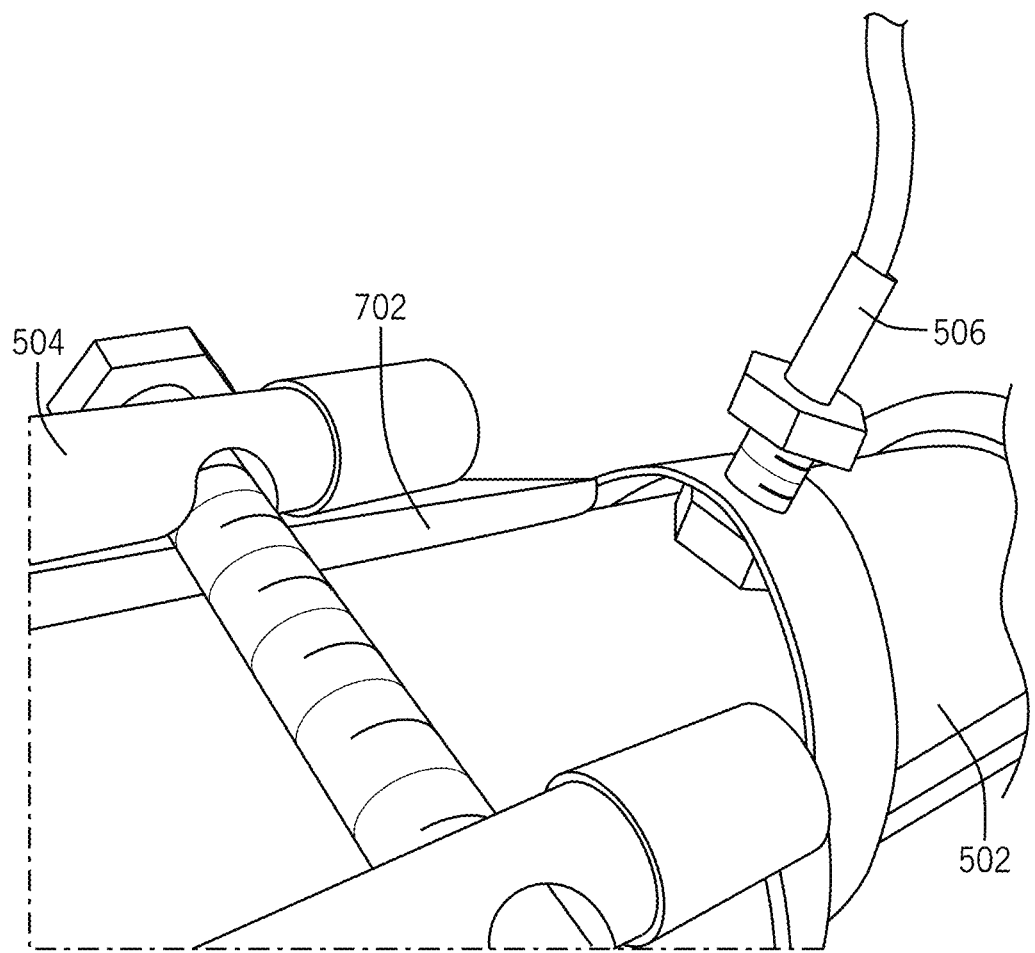
FIG. 7 is a partial perspective view of the heating chamber and a heating element of the standalone herb processing, vaporizing, and administration apparatus of FIG. 1, in embodiments.

FIG. 7 is a partial perspective view of the heating chamber 502 and a heating element 702 of the standalone herb processing, vaporizing, and administration apparatus of FIG. 1, in embodiments. The heating element 702 is a band heater, which is in contact with the heating chamber 502, so that it may heat the heating chamber when powered by electricity. A controller or processor, such as the controller 518, may control when and how much power is sent to the heating element 702, and thereby control how hot the heating chamber 502 becomes, as measured by the thermocouple 506. The heating element 702 is held in place by the band heater clamp 504.

Figure 8:
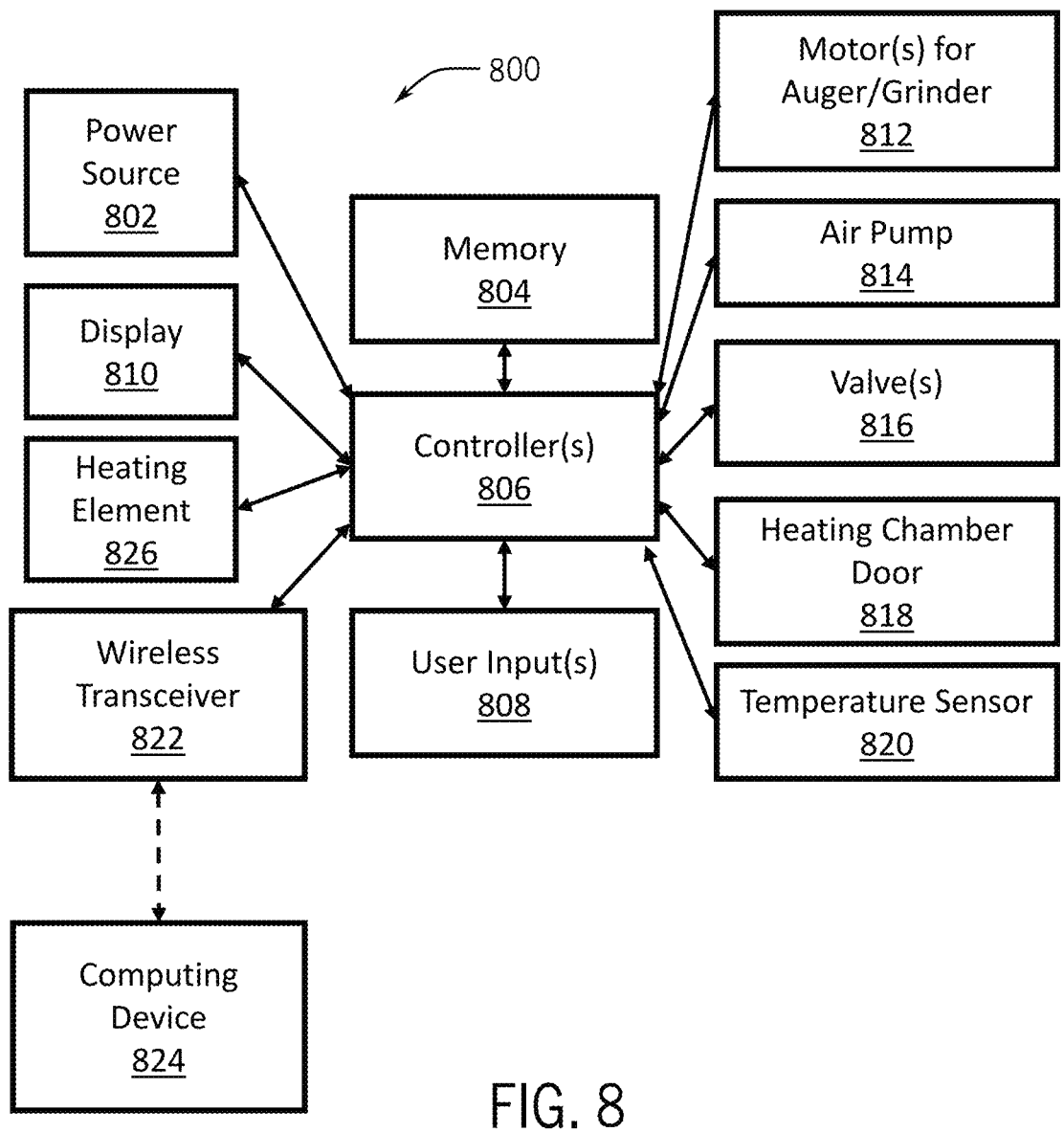
FIG. 8 is a schematic illustrating an example standalone herb processing, vaporizing, and administration system, in embodiments.

FIG. 8 is a schematic illustrating an example standalone herb processing, vaporizing, and administration system 800, in embodiments. In particular, the standalone herb processing, vaporizing, and administration system 800 includes a power source 802, a memory 804, controller(s) 806, user input(s) 808, a display 810, motor(s) for an screw feeder and/or grinder, an air pump 814, a valve 816, a heating chamber door 818, a temperature sensor 820, a wireless transceiver 822, a computing device 824, and a heating element 826. The power source 802 may provide power to the entire system 800, and therefore may also be connected directly to other aspects of the system 800 shown in FIG. 8, even though such direct connections are not shown. Other power sources may also be used, or transformers may be used, to condition power for various components of the system 800 that may use different types of power (e.g., alternating current vs. direct current, different voltages, different frequencies, different amperages, etc.).

The controller(s) 806 may be a computer processor that executes instructions stored on the memory 804 to control different aspects of the system 800. For example, the controller(s) 806 may receive an input from the user input(s) 808 or from the computing device 824 via the wireless transceiver 822. The wireless transceiver 822 may be in or on a vaporizer device so that the vaporizer device may wirelessly communicate with other devices (e.g., the computing device 824).

As described herein, the user input(s) 808 may be any type of input, such as a touchscreen, buttons, eye movement or other visual tracking using a camera or other sensor (e.g., for gesture tracking and control), a microphone for voice control, or any other type of user input device. Using the user input(s) 808, the user may cause the vaporizer device to turn on and create vapor, enter a cleaning mode, adjust a temperature to which the herb should be heated, adjust an amount of time the herb should be heated, enter a predetermined vaporize mode (e.g., a certain amount of time and temperature preconfigured for a particular type of herb), adjust the speed at which a motor in the system turns, adjust a speed at which an air pump moves air and vapor within the system or outputting air and vapor from the system, or for any other function. Any function that may be controllable using the user input(s) 808 may also be controllable using the computing device 824, for example through an application, API, or any other method for controlling a device remotely. The wireless communications between the wireless transceiver 822 and the computing device 824 may be made over WiFi, Bluetooth, infrared, and/or any other type of wireless communication.

In various embodiments, the vaporizer devices herein may have a one input operation mode. In such an operation mode, a single input may be all that is required from a user to cause herb to be vaporized. For example, after herb is loaded into a hopper, any type of input via the user input(s) 808 described herein may be made, and the system may automatically grind, heat, and move vapor to an output device for consumption by a user. Thus, the system advantageously requires little interaction from a user to vaporize herb.

The controller(s) 806 may further execute instructions to turn on, turn off, or adjust a speed of the motor(s) for an screw feeder and/or grinder 812. In various embodiments, more than one motor may be used in the system 800 and controlled using the controller(s) 806. The controller(s) 806 may further execute instructions to turn on, turn off, or adjust a speed of the air pump 814 that moves air and/or vapor within the system 800 and to an output of the system 800. The controller(s) 806 may further execute instructions for opening or closing the valve(s) 816. The valve(s) 816 may be or may include a valve such as the valve 520 of FIG. 5 described above. As such, the controller(s) 806 may control the valve(s) 816 to control output of air and vapor from the system as described herein.

Similarly, the controller(s) 806 may moveably control a heating chamber door 818. The heating chamber door 818 may be a moveable sealing component as described herein, or may be any type of louver or moveable component for restricting or permitting movement of vapor, fluid, herb, etc. between different internal components of the system 800 as described herein. In various embodiments, more than one door or moveable component may be used as desired.

The controller may also send signals to the display 810 to indicate a status of the system, such as currently cleaning, currently in standby, currently vaporizing, currently grinding, a temperature of the heating chamber, a temperature of vapor within the system, whether the air pump is on or off, etc. Other output devices than a display may also be used, such as a speaker that may emit sound when vaporizing or cleaning is complete, or that emits voice audio with instructions for operation to a user.

The controller may also receive signals from a temperature sensor 820, such as the thermocouple 506 of FIG. 5. In this way, the controller(s) 806 may determine the temperature of a heating chamber as described herein and send a signal to the heating element 826 to cause the heating chamber to heat or cool to a desired temperature. In various embodiments, more than one temperature sensor may be used so that the temperature of different portions of a vaporizer may be monitored and/or used to determine how to control various aspects of the system 800. For example, a temperature sensor may also be placed within a chamber where air and/or vapor is pumped from the heating chamber to an output device (e.g., at the spent herb outlet 510 of FIG. 5). Such a temperature sensor may be used to monitor air temperature that may be pumped to an output device to ensure the air is not too hot for a user. If the air is above a predetermined threshold temperature, the controller(s) 806 may wait until the air drops to a predetermined temperature or drops below the predetermined threshold temperature before pumping air to an output device for the safety of the user. Such thresholds may be manually set by the user or may be preconfigured upon manufacture and setup of the vaporizer device. Although FIG. 8 shows various components of just one example vaporizer device, different, additional, or fewer components may be used in accordance with various embodiments described herein.

In some embodiments, the temperature settings of the vaporizer may be designed to correspond to desired compounds within an herb (e.g., different cannabinoid compounds) that a user desires to be vaporized. Accordingly, an experience may be customized based on different preset temperatures the heating element 826 may be heated to. Such temperature settings may be associated with different types of experiences that are displayed or otherwise presented to a user, such as calm, reduce anxiety/depression, pain relief, or any other preset functions/settings. The user may select such a preset function using one or more user input(s) 808, which may then automatically process and vaporize the herb according to the preconfigured experience settings.

Figure 9:
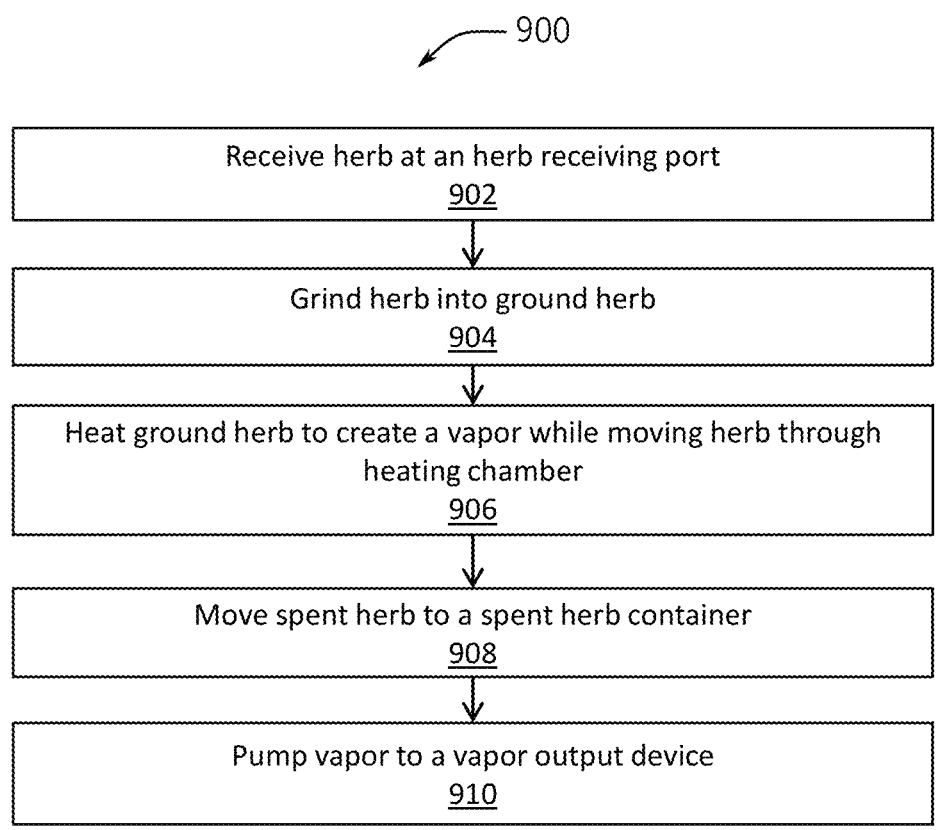
FIG. 9 is a flow chart illustrating an example method of using a standalone herb processing, vaporizing, and administration apparatus to create a vapor from herb, in embodiments.

FIG. 9 is a flow chart illustrating an example method 900 of using a standalone herb processing, vaporizing, and administration apparatus to create a vapor from herb, in embodiments. In an operation 902, herb is received at an herb receiving port (e.g., the herb receiving port 176 of FIGS. 1 and 5). In an operation 904, the herb is ground by a grinder into ground herb. The grinder may be, for example, the grinder 208 of FIG. 2.

In an operation 906, the ground herb is heated to create a vapor while the herb is moved through a heating chamber (e.g., the heating chamber 502 of FIG. 5). In an operation 908, spent herb (e.g., ground herb that has been thoroughly heated and vaporized), is moved from the heating chamber to a spent herb container for storage. The spent herb container may be sized to hold many uses/sessions worth of spent herb, so that the spent herb container need only be emptied periodically. In an operation 910, the vapor created may be pumped to a vapor output device, such as a mask, ventilator adapter, whip, balloon, bag, etc.

Figure 10:
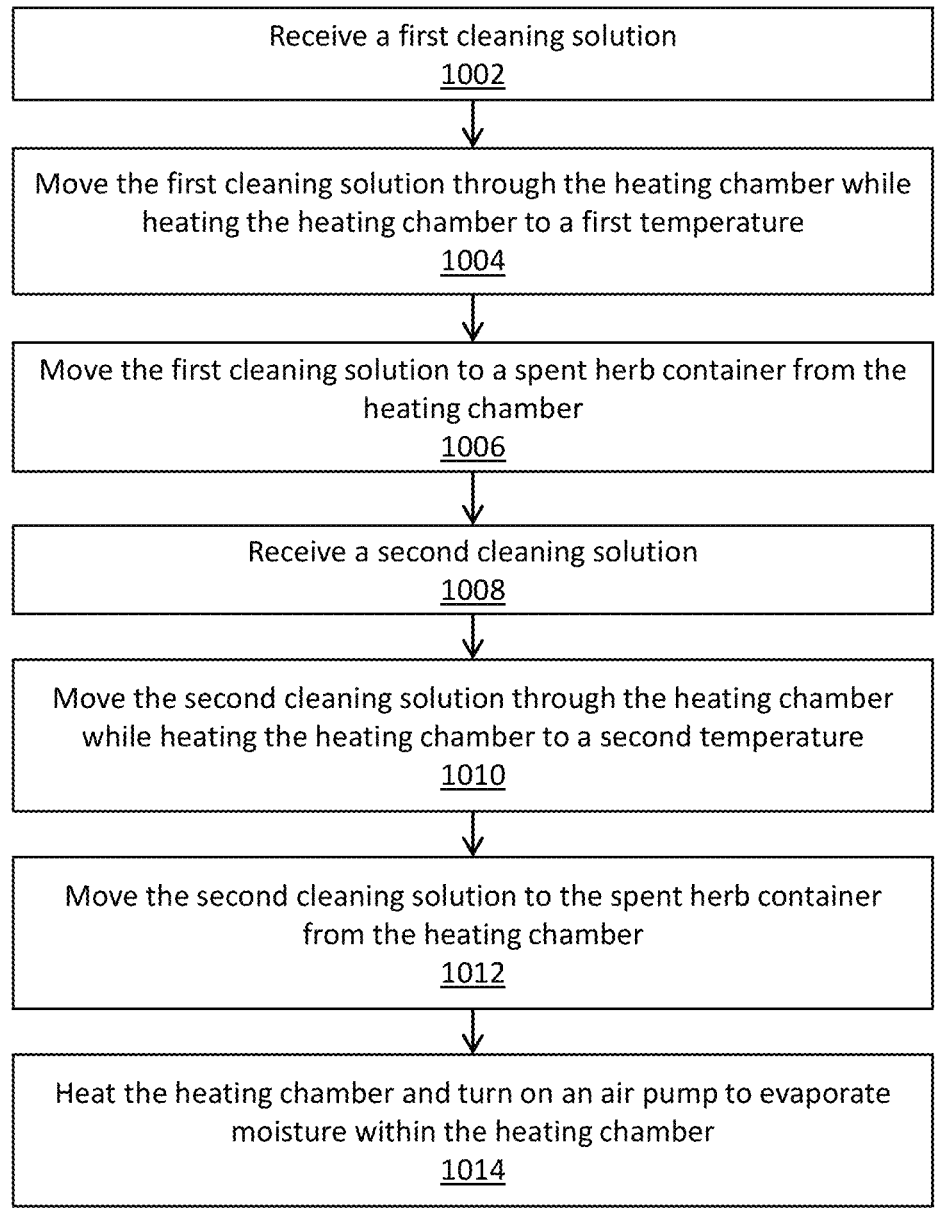
FIG. 10 is a flow chart illustrating an example method of cleaning standalone herb processing, vaporizing, and administration apparatus, in embodiments.

FIG. 10 is a flow chart illustrating an example method 1000 of cleaning standalone herb processing, vaporizing, and administration apparatus, in embodiments. Like the apparatuses, methods, and systems described herein for vaporizing herb using a vaporizing device, a cleaning process of such a vaporizing device may also be automated to reduce interaction required to clean the vaporizer device. Such cleaning methods may be advantageous, for example, for a user with limited mobility and/or dexterity who may not be able to adequately perform all of the manual steps of cleaning a vaporizer device. The example method 1000 describes a cleaning method that uses two different cleaning solutions, one at a time, to adequately clean a vaporizer device. However, methods using a single cleaning solution or using more than two cleaning solutions may be used according to various embodiments. In some embodiments, a cleaning process may involve one or more cleaning solutions and one or more other fluids that are not cleaning solutions, such as water to rinse a system before, after, and/or during cleaning.

Such cleaning methods may use fluids that are manually added to the system whenever cleaning is desired or required, or the vaporizer devices described herein may optionally have reservoirs for storing one or more fluids used for cleaning, so that the system may be cleaned without manually adding fluids for cleaning each time. In some embodiments, if water is used for example, the vaporizer may be connected to a water pipe, faucet, or other water line in a house or other structure so that the vaporizer may consistently be connected to a supply of water. In this way, the interaction required by a user to clean the vaporizer device may be further reduced.

In an operation 1002 of the method 1000, a first cleaning solution is received. The first cleaning solution may be received by a first cleaning solution container configured especially for the first cleaning solution. In other embodiments, the first cleaning solution may be added to an opening in a vaporizer device that is not solely for the first cleaning solution, such as the hopper 172 of the vaporizer device 170 in FIG. 1.

In an operation 1004, the first cleaning solution is moved through the heating chamber while the heating chamber is heated to a first temperature. Optionally, the heating chamber may not be heated while the first cleaning solution is in the heating chamber. In addition, to aid in the cleaning and contacting of surfaces in the heating chamber with the first cleaning solution, the screw feeder or other moveable aspect within the heating chamber may be actuated to circulate the first cleaning solution within the heating chamber.

In an operation 1006, the first cleaning solution is moved from the heating chamber to a spent herb container. In some embodiments, a separate spent cleaning solution chamber may receive and store any spent cleaning solution to, instead of it being moved to the same container as spent herb. Optionally, the heating chamber may be heated after the first cleaning solution is moved out of the heating chamber to evaporate remaining liquid within the heating chamber. Similarly, the air pump may be switched on to move air through the heating chamber to assist in evaporating liquid within the heating chamber.

In an operation 1008, a second cleaning solution is received. Using multiple cleaning solutions may be beneficial for efficiently cleaning a vaporizer device. Like the first cleaning solution, the second cleaning solution may be input into a dedicated second cleaning solution receiving container, or may be added to an area that receives herb and/or other cleaning solutions or fluids. In an operation 1010, the second cleaning solution is moved through the heating chamber while the heating chamber is heated to a desired temperature. The desired temperature may be different than a temperature used with the first cleaning solution based on characteristics or properties of the two cleaning solutions. Optionally, the screw feeder or other agitating device within the heating chamber may be moved to circulate the second cleaning solution within the heating chamber. The second cleaning solution may not be added to the heating chamber until after the first cleaning solution has been removed from the heating chamber, or the first and second cleaning solutions may be added to the heating chamber at the same time.

In an operation 1012, the second cleaning solution is moved from the heating chamber to the spent herb container (or other output for cleaning solution). In an operation 1014, after the second cleaning solution is moved out of the heating chamber, the heating chamber is heated and/or the air pump is turned on to evaporate moisture from the cleaning solutions that may still be in the heating chamber. Moisture in the heating chamber may negatively impact how herb is vaporized, so the system evaporates excess moisture before entering a vaporizing mode again. In some embodiments, the operation 1014 may last for a predetermined amount of time, until the heating chamber reaches a certain temperature, until the heating chamber is a certain temperature for a predetermined amount of time, or any other method for properly evaporating moisture within the heating chamber. In some embodiments, the vaporizing device may include a moisture or humidity sensor within the heating chamber, air pump, tubing, spent herb outlet, etc. to measure a moisture quantity in the air from or within the heating chamber. Such a sensor may be used to run the evaporation cycle for as long as needed to remove moisture from the heating chamber to an acceptable degree.

A moisture or humidity sensor may also be used to determine if herb in the heating chamber is not yet completely spent. For example, if herb is not spent, it may be kept in the heating chamber and used during the next session. The moisture sensor may indicate a humidity or moisture level that indicates whether the herb is spent or not. Thus, the controller may determine whether to keep herb in the heating chamber for a subsequent use or move the herb to a spent herb container if the moisture level is below a predetermined threshold indicating that the herb is spent.

Because the heating chamber may be angled downward as shown in and described with respect to FIG. 5 above, the cleaning solution may advantageously flow through the system from top to bottom, stopping only when moveable seals, doors, louvers, etc. block it from flowing. Advantageously, this can provide for a system with few moving parts that may be very easily operated, including by a user with limited mobility or dexterity. In other words, because the first end of a heating chamber may be oriented closer to the top of a standalone herb processing, vaporizing, and administration apparatus than a second end of the heating chamber, cleaning solution may be acted upon by gravity to move from the first end of the heating chamber to the second end of the heating chamber. Similarly, the spent herb container or other container in which waste herb and/or cleaning solution is stored may be located below the second end of the heating chamber, such that gravity may also act to move cleaning solution and/or herb into the waste herb or cleaning solution storage containers (when the moveable sealing doors, louvers, etc. are controlled to permit such movement as desired). In this way, a moveable sealing component may keep the cleaning solution in the heating chamber during cleaning (and prevent the cleaning solution from moving to a spent herb container), but may permit the movement of the cleaning solution to the spent herb container or other waste storage container once the moveable sealing component is opened or otherwise unsealed.

While embodiments related to specific easy-to-use, automated systems for dispensing vapor from herb are described herein other systems may also be used to dispense vapor to a user in such automated ways that require little interaction from an end-user. For example, herb may be placed on a rotating disk or other movement/conveyor system that moves the herb to a grinder, then to a heater, and then to an open slot for waste once the herb is spent. Other systems may utilize oils or waxes for vaporizing. For example, a pressure driven fluidics system may be used to transport and move oil or wax through different components of a vaporizer. As just one example, oil or wax may be put in a syringe that is placed in a motorized screw driven syringe pump for dispensing the oil or wax and driving flow of the oil or wax. The oil or wax may be dispensed to a metal tube with a portion that has a band heater for heating the oil or wax into vapor. Accordingly, various embodiments for automatically dispensing vapor to a user may be used as described herein.

Figure 11:
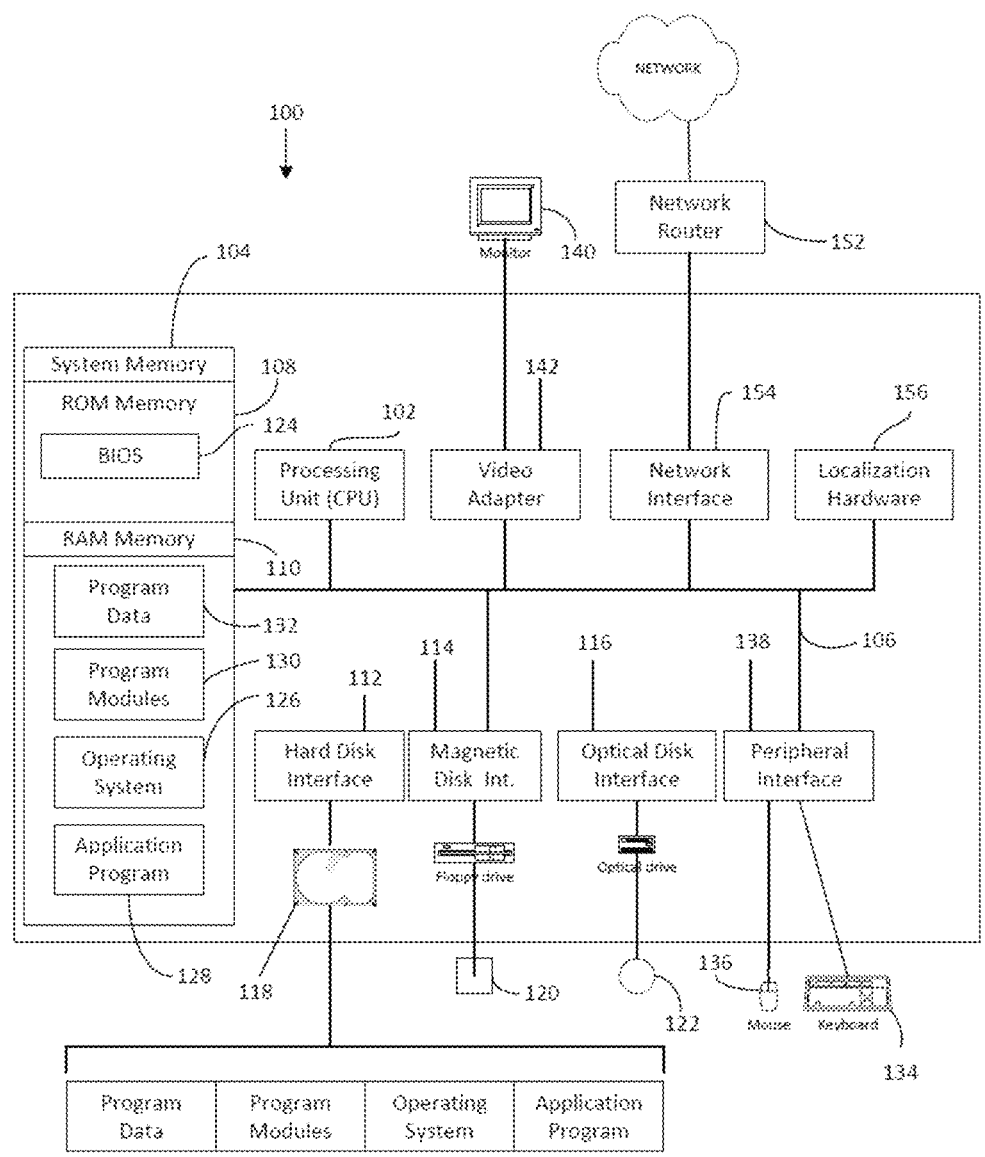
FIG. 11 is a diagrammatic view of an example user computing environment, in embodiments.

FIG. 11 is a diagrammatic view of an illustrative computing system that includes a general purpose computing system environment 120, such as a desktop computer, laptop, smartphone, tablet, or any other such device having the ability to execute instructions, such as those stored within a non-transient, computer-readable medium. Furthermore, while described and illustrated in the context of a single computing system 120, those skilled in the art will also appreciate that the various tasks described hereinafter may be practiced in a distributed environment having multiple computing systems 120 linked via a local or wide-area network in which the executable instructions may be associated with and/or executed by one or more of multiple computing systems 120.

In its most basic configuration, computing system environment 120 typically includes at least one processing unit 122 and at least one memory 124, which may be linked via a bus 126. Depending on the exact configuration and type of computing system environment, memory 124 may be volatile (such as RAM 130), non-volatile (such as ROM 128, flash memory, etc.) or some combination of the two. Computing system environment 120 may have additional features and/or functionality. For example, computing system environment 120 may also include additional storage (removable and/or non-removable) including, but not limited to, magnetic or optical disks, tape drives and/or flash drives. Such additional memory devices may be made accessible to the computing system environment 120 by means of, for example, a hard disk drive interface 132, a magnetic disk drive interface 134, and/or an optical disk drive interface 136. As will be understood, these devices, which would be linked to the system bus 126, respectively, allow for reading from and writing to a hard disk 138, reading from or writing to a removable magnetic disk 140, and/or for reading from or writing to a removable optical disk 142, such as a CD/DVD ROM or other optical media. The drive interfaces and their associated computer-readable media allow for the nonvolatile storage of computer readable instructions, data structures, program modules and other data for the computing system environment 120. Those skilled in the art will further appreciate that other types of computer readable media that can store data may be used for this same purpose. Examples of such media devices include, but are not limited to, magnetic cassettes, flash memory cards, digital videodisks, Bernoulli cartridges, random access memories, nanodrives, memory sticks, other read/write and/or read-only memories and/or any other method or technology for storage of information such as computer readable instructions, data structures, program modules or other data. Any such computer storage media may be part of computing system environment 120.

A number of program modules may be stored in one or more of the memory/media devices. For example, a basic input/output system (BIOS) 144, containing the basic routines that help to transfer information between elements within the computing system environment 120, such as during start-up, may be stored in ROM 128. Similarly, RAM 130, hard drive 138, and/or peripheral memory devices may be used to store computer executable instructions comprising an operating system 146, one or more applications programs 148 (such as a Web browser and/or other applications that execute the methods and processes of this disclosure), other program modules 150, and/or program data 152. Still further, computer-executable instructions may be downloaded to the computing environment 120 as needed, for example, via a network connection.

An end-user, e.g., a customer, retail associate, and the like, may enter commands and information into the computing system environment 120 through input devices such as a keyboard 154 and/or a pointing device 156. While not illustrated, other input devices may include a microphone, a joystick, a game pad, a scanner, etc. These and other input devices would typically be connected to the processing unit 122 by means of a peripheral interface 158 which, in turn, would be coupled to bus 126. Input devices may be directly or indirectly connected to processor 122 via interfaces such as, for example, a parallel port, game port, firewire, or a universal serial bus (USB). To view information from the computing system environment 120, a monitor 160 or other type of display device may also be connected to bus 26 via an interface, such as via video adapter 162. In addition to the monitor 160, the computing system environment 120 may also include other peripheral output devices, not shown, such as speakers and printers.

The computing system environment 120 may also utilize logical connections to one or more computing system environments. Communications between the computing system environment 120 and the remote computing system environment may be exchanged via a further processing device, such a network router 152, that is responsible for network routing. Communications with the network router 152 may be performed via a network interface component 154. Thus, within such a networked environment, e.g., the Internet, World Wide Web, LAN, or other like type of wired or wireless network, it will be appreciated that program modules depicted relative to the computing system environment 120, or portions thereof, may be stored in the memory storage device(s) of the computing system environment 120.

The computing system environment 120 may also include localization hardware 156 for determining a location of the computing system environment 120. In embodiments, the localization hardware 156 may include, for example only, a GPS antenna, an RFID chip or reader, a WiFi antenna, or other computing hardware that may be used to capture or transmit signals that may be used to determine the location of the computing system environment 120.

While this disclosure has described certain embodiments, it will be understood that the claims are not intended to be limited to these embodiments except as explicitly recited in the claims. On the contrary, the instant disclosure is intended to cover alternatives, modifications and equivalents, which may be included within the spirit and scope of the disclosure. Furthermore, in the detailed description of the present disclosure, numerous specific details are set forth in order to provide a thorough understanding of the disclosed embodiments. However, it will be obvious to one of ordinary skill in the art that systems and methods consistent with this disclosure may be practiced without these specific details. In other instances, well known methods, procedures, components, and circuits have not been described in detail as not to unnecessarily obscure various aspects of the present disclosure.

Some portions of the detailed descriptions of this disclosure have been presented in terms of procedures, logic blocks, processing, and other symbolic representations of operations on data bits within a computer or digital system memory. These descriptions and representations are the means used by those skilled in the data processing arts to most effectively convey the substance of their work to others skilled in the art. A procedure, logic block, process, etc., is herein, and generally, conceived to be a self-consistent sequence of steps or instructions leading to a desired result. The steps are those requiring physical manipulations of physical quantities. Usually, though not necessarily, these physical manipulations take the form of electrical or magnetic data capable of being stored, transferred, combined, compared, and otherwise manipulated in a computer system or similar electronic computing device. For reasons of convenience, and with reference to common usage, such data is referred to as bits, values, elements, symbols, characters, terms, numbers, or the like, with reference to various embodiments of the present invention.

It should be borne in mind, however, that these terms are to be interpreted as referencing physical manipulations and quantities and are merely convenient labels that should be interpreted further in view of terms commonly used in the art. Unless specifically stated otherwise, as apparent from the discussion herein, it is understood that throughout discussions of the present embodiment, discussions utilizing terms such as "determining" or "outputting" or "transmitting" or "recording" or "locating" or "storing" or "displaying" or "receiving" or "recognizing" or "utilizing" or "generating" or "providing" or "accessing" or "checking" or "notifying" or "delivering" or the like, refer to the action and processes of a computer system, or similar electronic computing device, that manipulates and transforms data. The data is represented as physical (electronic) quantities within the computer system's registers and memories and is transformed into other data similarly represented as physical quantities within the computer system memories or registers, or other such information storage, transmission, or display devices as described herein or otherwise understood to one of ordinary skill in the art.

What is claimed is:

1. A standalone herb processing, vaporizing, and administration apparatus comprising:
    an herb receiving port configured to receive herb;
    a grinder configured to grind the herb received at the herb receiving port into ground herb;
    a heating chamber configured to receive the ground herb, wherein:
        the heating chamber is configured to heat the ground herb, to thereby create a vapor,
        the heating chamber comprises a first end at which the ground herb is initially received, and a second end at which the ground herb is output from the heating chamber,
        the first end of the heating chamber is positioned closer to a top of the standalone herb processing, vaporizing, and administration apparatus than the second end of the heating chamber, such that the ground herb generally moves in at least a partially downward direction as it travels through the heating chamber;
    a screw feeder positioned within the heating chamber, the screw feeder configured to rotate and thereby move the ground herb within the heating chamber;
    an air pump configured to pump the vapor out of the heating chamber to a vapor output device;
    and a valve positioned along an airway between the heating chamber and the vapor output device, wherein the valve is configured to permit air and the vapor to move from the heating chamber to the vapor output device only while the air pump is activated.

2. The standalone herb processing, vaporizing, and administration apparatus of claim 1, wherein the screw feeder is configured to rotate at a variety of different speeds to move the ground herb within the heating chamber.

3. The standalone herb processing, vaporizing, and administration apparatus of claim 1, wherein the valve comprises an electrically controllable valve configured to switch between an open and a closed position, and wherein the electrically controllable valve is further configured to:
    permit air and the vapor to move from the heating chamber to the vapor output device while the valve is open, prevent air and the vapor from moving from the vapor output device to the heating chamber while the valve is open, and prevent air and the vapor from moving past the valve in either direction while the valve is closed.

4. The standalone herb processing, vaporizing, and administration apparatus of claim 1, wherein:

the heating chamber is configured to receive a cleaning solution at the first end of the heating chamber; and because the first end of the heating chamber is oriented closer to the top of the standalone herb processing, vaporizing, and administration apparatus than the second end of the heating chamber, the cleaning solution is acted upon by gravity to move from the first end to the second end.

5. An apparatus comprising:

a heating chamber configured to receive ground herb, wherein:

the heating chamber is configured to heat the ground herb, the heating chamber comprises a first end at which the ground herb is initially received, and a second end at which the ground herb is output from the heating chamber, and the first end of the heating chamber is positioned closer to a top of the apparatus than the second end of the heating chamber, such that the ground herb generally moves in at least a partially downward direction as it travels through the heating chamber; and a screw feeder positioned within the heating chamber, the screw feeder configured to rotate and thereby move the ground herb within the heating chamber.

6. The apparatus of claim 5, wherein the screw feeder comprises a screw feeder drill bit or a screw conveyor.

7. The apparatus of claim 5, wherein the screw feeder serves to move the ground herb from the first end of the heating chamber to the second end of the heating chamber, and wherein the second end of the heating chamber is connected to a spent herb container.

8. The apparatus of claim 5, wherein the heating chamber is cylindrically shaped.

9. The apparatus of claim 5, wherein the screw feeder is configured to rotate at a variety of different speeds.

10. An apparatus comprising:

a heating chamber configured to receive ground herb, wherein:

the heating chamber is configured to heat the ground herb;

the heating chamber comprises a first end at which the ground herb is initially received, and a second end at which the ground herb is output from the heating chamber;

the first end of the heating chamber is positioned closer to a top of the standalone herb processing, vaporizing, and administration apparatus than the second end of the heating chamber; and the heating chamber is configured to receive a cleaning solution;

a spent herb container at the second end of the heating chamber, configured to receive the ground herb after it has passed through the heating chamber; and a moveable sealing component at the second end of the heating chamber configured to:

form a seal at the second end of the heating chamber to prevent the cleaning solution from moving from the heating chamber to the spent herb container during a cleaning process of the apparatus and move to unseal the second end of the heating chamber to permit the cleaning solution from within the heating chamber to move to the spent herb container when the cleaning process has concluded.

11. The apparatus of claim 10, further comprising a screw feeder positioned within the heating chamber and configured to rotate, to thereby move the ground herb within the heating chamber.

12. The apparatus of claim 10, further comprising a first cleaning solution receiving container configured to receive a first cleaning solution and a second cleaning solution receiving container configured to receive a second cleaning solution, wherein the apparatus, during a cleaning process, is configured to:

move the first cleaning solution from the first cleaning solution receiving container to the heating chamber;

heat the heating chamber to a first predetermined temperature for a first predetermined amount of time while the first cleaning solution is in the heating chamber;

move the first cleaning solution from the heating chamber to a spent herb container located at the second end of the heating chamber;

after the first cleaning solution is moved from the heating chamber to the spent herb container, move the second cleaning solution from the second cleaning solution receiving container to the heating chamber;

heat the heating chamber to a second predetermined temperature for a second predetermined amount of time while the second cleaning solution is in the heating chamber; and move the second cleaning solution from the heating chamber to the spent herb container.

13. The apparatus of claim 12, wherein after the second cleaning solution is moved from the heating chamber to the spent herb container during the cleaning process, the apparatus is further configured to:

heat the heating chamber to assist in evaporating residual moisture from one or more surfaces within the heating chamber; and turn on an air pump to move air through the heating chamber to further assist in evaporating and removing the residual moisture from the one or more surfaces within the heating chamber.

14. An apparatus comprising:

a heating chamber configured to receive ground herb and heat the ground herb, to thereby create a vapor;

an air pump configured to pump the vapor out of the heating chamber to a vapor output device; and an electrically controllable valve positioned along an airway between the heating chamber and the vapor output device and configured to switch between an open and a closed position, wherein the electrically controllable valve is further configured to:

permit air and the vapor to move from the heating chamber to the vapor output device only while the air pump is activated, permit air and the vapor to move from the heating chamber to the vapor output device while the valve is open, prevent air and the vapor from moving from the vapor output device to the heating chamber while the valve is open, and prevent air and the vapor from moving past the valve in either direction while the valve is closed.

15. The apparatus of claim 14, further comprising a controller configured to control the electrically controllable valve and the air pump to Response to Non-Final Office Action simultaneously actuate, such that air and the vapor moves from the heating chamber to the vapor output device only while the air pump is activated.

16. The apparatus of claim 14, wherein the controller is further configured to:
   control a heating element of the heating chamber to heat the heating chamber to a predetermined temperature;
   control a screw feeder within the heating chamber to move the ground herb through the heating chamber, such that the ground herb is in the heating chamber for a predetermined amount of time.

17. The apparatus of claim 14, wherein the vapor output device is configured to expel air and the vapor into at least one of a balloon, a bag, a whip, a face mask, or a ventilator adaptor.

* * * * *